United States Patent
Meyers et al.

(10) Patent No.: US 9,541,223 B2
(45) Date of Patent: Jan. 10, 2017

(54) TWO-SHOT TUBE RETENTION POCKET TUBE CLAMP, MOLD AND PROCESS

(71) Applicant: NEWFREY LLC, Newark, DE (US)

(72) Inventors: Jason A. Meyers, Shelby Township, MI (US); Roger E. Pilon, New Baltimore, MI (US); Tien T. Diep, West Bloomfield, MI (US)

(73) Assignee: NEWFREY LLC, New Britain, CT (US)

( * ) Notice: Subject to any disclaimer, the term of this patent is extended or adjusted under 35 U.S.C. 154(b) by 0 days.

(21) Appl. No.: 14/319,830

(22) Filed: Jun. 30, 2014

(65) Prior Publication Data

US 2015/0377387 A1     Dec. 31, 2015

(51) Int. Cl.
*F16L 3/22* (2006.01)
*F16L 3/13* (2006.01)
(Continued)

(52) U.S. Cl.
CPC .............. *F16L 3/13* (2013.01); *B29C 45/0017* (2013.01); *B29C 45/12* (2013.01);
(Continued)

(58) Field of Classification Search
CPC .............. H02G 3/32; H02G 3/30; H02G 3/26; H02G 3/22; F16L 3/00; F16L 3/08; F16L 3/12; F16L 3/1211; F16L 3/1236; F16L 3/22; F16L 3/02; F16L 3/137; F16L 3/223; F16L 3/23; F16L 3/233; F16L 3/237; H01R 13/518; A61M 5/1418
(Continued)

(56) References Cited

U.S. PATENT DOCUMENTS 2,438,523 A * 3/1948 Tinnerman ................... 248/74.3
4,467,988 A    8/1984 Kraus
(Continued)

FOREIGN PATENT DOCUMENTS

| DE | 60117115 T2 | 8/2006 |
|---|---|---|
| EP | 1013978 A2 | 6/2000 |
| WO | WO2011/028705 A1 | 3/2011 |

OTHER PUBLICATIONS

European Search Report dated Nov. 11, 2015 in corresponding European Patent Application No. 15169572.3.

*Primary Examiner* — Brian Mattei
*Assistant Examiner* — Taylor Morris
(74) *Attorney, Agent, or Firm* — Harness, Dickey & Pierce, P.L.C.

(57) ABSTRACT

A first shot body member includes a pair of side walls, a semi-circular sleeve positioned between the pair of side walls to define a portion of a longitudinal pocket, and a pair of deflecting wings. Each deflecting wing is coupled to one of the side walls at a corner. A second shot isolation member of an elastically resilient second material is bonded to portions of an interior surface of the longitudinal pocket defined by each of: the semi-circular sleeve, each of the pair of side walls, each of the pair of corners, and each of the pair of wings. Mold members can include supporting surfaces to support interior and exterior portions of the wing during the second shot molding operation, while leaving an exposed interior bonding surface that defines a portion of the second shot molding cavity. Related methods are further disclosed.

23 Claims, 9 Drawing Sheets

(51) Int. Cl.

| | | |
|---|---|---|
| *B29C 45/00* | (2006.01) | |
| *B29C 45/12* | (2006.01) | |
| *B29C 45/16* | (2006.01) | |
| *B29C 45/26* | (2006.01) | |
| *F16L 55/035* | (2006.01) | |
| *B60R 16/02* | (2006.01) | |
| *F16L 3/223* | (2006.01) | |
| *F16L 3/16* | (2006.01) | |
| *F16L 3/00* | (2006.01) | |
| *F16L 3/08* | (2006.01) | |
| *F16L 3/12* | (2006.01) | |
| *F16L 3/02* | (2006.01) | |
| *H02G 3/32* | (2006.01) | |
| *H02G 3/30* | (2006.01) | |
| *A61M 5/14* | (2006.01) | |
| *H02G 3/22* | (2006.01) | |
| *B29L 9/00* | (2006.01) | |
| *B29L 31/00* | (2006.01) | |

(52) U.S. Cl.
CPC ...... *B29C 45/1671* (2013.01); *B29C 45/1675* (2013.01); *B29C 45/2628* (2013.01); *B60R 16/0215* (2013.01); *F16L 3/22* (2013.01); *F16L 3/223* (2013.01); *F16L 55/035* (2013.01); *A61M 5/1418* (2013.01); *B29C 45/1676* (2013.01); *B29C 2045/1673* (2013.01); *B29K 2995/0002* (2013.01); *B29K 2995/0046* (2013.01); *B29L 2009/00* (2013.01); *B29L 2031/727* (2013.01); *F16L 3/00* (2013.01); *F16L 3/02* (2013.01); *F16L 3/08* (2013.01); *H02G 3/22* (2013.01); *H02G 3/30* (2013.01); *H02G 3/32* (2013.01)

(58) Field of Classification Search
USPC .......................... 248/55, 68.1, 73, 74.1, 74.2
See application file for complete search history.

(56) References Cited

U.S. PATENT DOCUMENTS

| | | | | |
|---|---|---|---|---|
| 4,511,107 A | * | 4/1985 | Funk | F16L 3/22 248/49 |
| 4,614,321 A | * | 9/1986 | Andre | 248/74.2 |
| 4,743,422 A | | 5/1988 | Kalriis-Nielsen et al. | |
| 5,257,768 A | | 11/1993 | Juenemann et al. | |
| 5,301,917 A | * | 4/1994 | Dyer | 248/74.2 |
| 5,460,342 A | | 10/1995 | Dore et al. | |
| 5,464,179 A | | 11/1995 | Ruckwardt | |
| 6,152,406 A | | 11/2000 | Denndou | |
| 6,641,093 B2 | | 11/2003 | Coudrais | |
| 6,752,950 B2 | | 6/2004 | Clarke | |
| 6,809,257 B2 | | 10/2004 | Shibuya | |
| 6,883,762 B2 | | 4/2005 | Miura et al. | |
| 6,899,304 B2 | * | 5/2005 | Bellmore et al. | 248/65 |
| 6,902,138 B2 | | 6/2005 | Vantouroux | |
| 6,926,237 B2 | | 8/2005 | Shereyk et al. | |
| 7,011,277 B2 | | 3/2006 | Mizukoshi et al. | |
| 7,201,351 B2 | * | 4/2007 | Stigler | 248/74.1 |
| 7,201,352 B2 | | 4/2007 | Kawai | |
| 7,207,528 B2 | * | 4/2007 | Kato | 248/55 |
| 7,267,307 B2 | | 9/2007 | Bauer | |
| 7,278,190 B2 | | 10/2007 | Fischer et al. | |
| 7,422,181 B2 | * | 9/2008 | Süßenbach | 248/56 |
| 7,600,725 B2 | * | 10/2009 | Mizukoshi | 248/74.1 |
| 7,658,350 B2 | | 2/2010 | Bauer | |
| 8,020,812 B2 | | 9/2011 | Matsuno et al. | |
| 8,157,223 B2 | * | 4/2012 | Stau | F16L 55/035 248/74.2 |
| 8,733,709 B2 | | 5/2014 | Meyers et al. | |
| 2002/0063189 A1 | | 5/2002 | Coudrais | |
| 2004/0188570 A1 | | 9/2004 | Bauer | |
| 2004/0217236 A1 | * | 11/2004 | Shibuya | 248/68.1 |
| 2004/0217314 A1 | | 11/2004 | Burian et al. | |
| 2005/0067548 A1 | | 3/2005 | Inoue | |
| 2005/0098688 A1 | | 5/2005 | Miarka et al. | |
| 2005/0116122 A1 | | 6/2005 | Nakanishi | |
| 2005/0284989 A1 | * | 12/2005 | Mizukoshi | 248/65 |
| 2006/0273226 A1 | | 12/2006 | Jatzke | |
| 2010/0025272 A1 | | 2/2010 | Stau et al. | |
| 2010/0207001 A1 | | 8/2010 | Smith et al. | |
| 2012/0298811 A1 | | 11/2012 | Ogawa et al. | |
| 2012/0317757 A1 | | 12/2012 | Risdale et al. | |
| 2013/0146720 A1 | | 6/2013 | Meyers et al. | |
| 2014/0259565 A1 | * | 9/2014 | Hirama | F16L 3/223 24/455 |

\* cited by examiner

TWO-SHOT TUBE RETENTION POCKET TUBE CLAMP, MOLD AND PROCESS

FIELD

The present disclosure relates to fasteners used in automobile vehicle service to retain and route tubing and electrical wiring, and related molds and molding processes.

BACKGROUND

This section provides background information related to the present disclosure which is not necessarily prior art.

Clips and fasteners are known which are used to retain tubular shaped objects such as metal or rubber tubing used for hydraulic, vacuum, fuel and similar services, and electrical wires, cables, and wire bundles in automobile vehicles. Vibration and sound transmitted from an upstream or downstream component of the vehicle can be transferred through the fastener to the body panel to which the fastener is connected, thereby inducing unwanted noise. Resilient material inserts can be provided using a two-shot molding process.

Known designs can provide less than optimal wing flexibility to facilitate maximum opening and centering capability during insertion of the tubular objects. In addition, known two-shot molds and processes can provide less than optimal support of the first shot component during the molding of the resilient second shot component.

SUMMARY

This section provides a general summary of the disclosure, and is not a comprehensive disclosure of its full scope or all of its features.

In accordance with a first aspect of the present disclosure, a tube retention fastener includes a body of a first polymeric material. The body includes a pair of side walls, a semi-circular sleeve positioned between the pair of side walls to define a portion of a longitudinal pocket, and a pair of deflecting wings. Each of the pair of deflecting wings is coupled to one of the pair of side walls at one of a pair of corners, respectively. Each deflecting wing extends toward a central plane passing through a longitudinal axis of the longitudinal pocket in a non-deflected position. The pair of side walls, the semi-circular sleeve, the pair of corners, and the pair of wings together define an interior surface of the longitudinal pocket. An isolation member of an elastically resilient second material is bonded to portions of an interior surface of the longitudinal pocket defined by: each of the semi-circular sleeve; each of the pair of side walls; each of the pair of corners; and each of the pair of wings.

In accordance with another aspect of the present disclosure, a two-shot tube retention fastener molding method is provided wherein the tube retention fastener includes a first shot body member having a pair of deflecting wings. Each of the pair of deflecting wings extends angularly toward each other from one of a pair of side walls, and a second shot isolation member is bonded along an interior surface of each of the pair of deflecting wings. The method includes molding the first shot body member, including the pair of deflecting wings. The second shot isolation member is molded while supporting an exterior wing surface of each of the pair of deflecting wings against a first mold surface and supporting a first interior wing surface portion of each of the pair of deflecting wings against a second mold surface, while leaving a second interior wing surface portion of each of the pair of deflecting wings unsupported to define a portion of a mold cavity of the second shot member extending from a distal end of the wing to the pair of side walls.

In accordance with another aspect of the present disclosure, a two-shot tube retention fastener mold includes a first mold member. A second mold member in combination with the first mold member defines a first shot member cavity that defines a first shot member having a pair of deflecting wings. Each of the pair of deflecting wings extends angularly toward each other from one of a pair of side walls. A semi-circular sleeve is positioned between the pair of side walls to define a longitudinal tube-holding pocket. A third mold member in combination with the first mold member and the first shot member defines a second shot member cavity that is partially defined by an exposed surface of the first shot member continuously extending from a distal end of a first one of the pair of deflecting wings, over the first one of the deflecting wings, over a first one of the pair of side walls, over the semi-circular sleeve, over a second one of the pair of side walls, over a second one of the pair of deflecting wings, to a distal end of the second one of the deflecting wings. When the first and third mold members are positioned for the second shot, the first mold member includes a first mold surface supporting an exterior wing surface portion of each of the pair of deflecting wings of the first shot member and a second mold surface supporting an interior wing surface portion while allowing for the continuously extending exposed surface over each deflecting wing.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Figure 1:
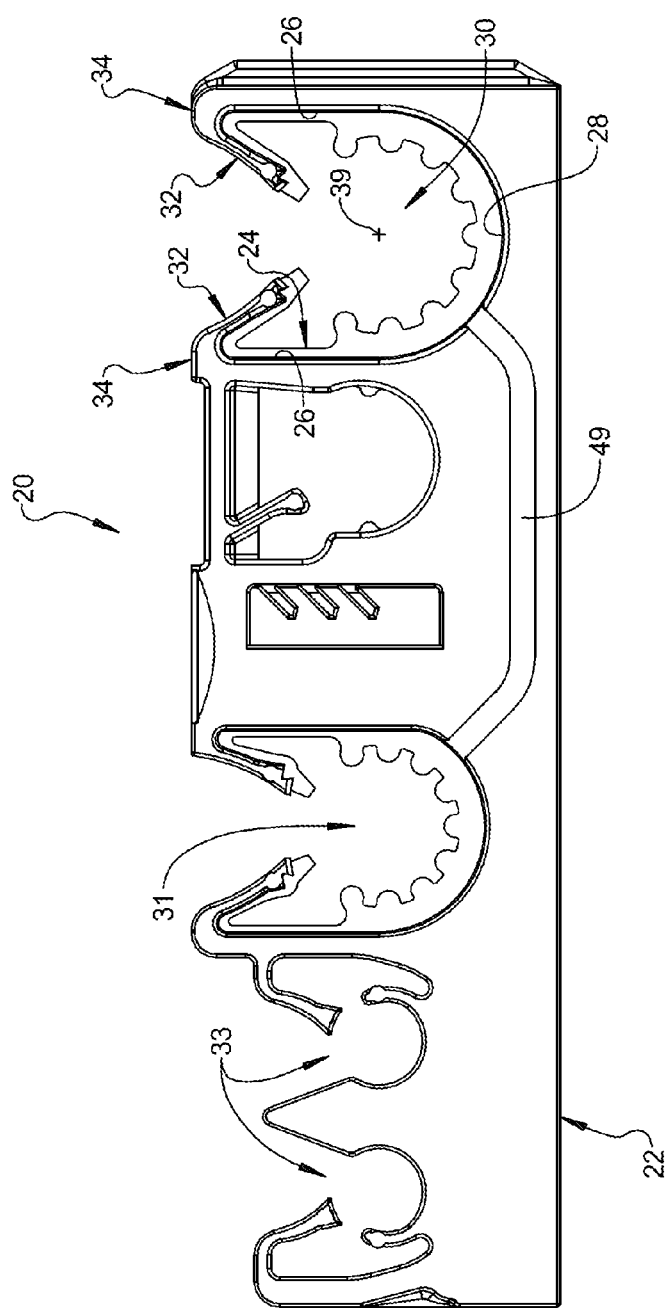
FIG. 1 is a front plan view of one exemplary embodiment of a two-shot tube retention pocket tube clamp in accordance with this disclosure.
Figure 2:
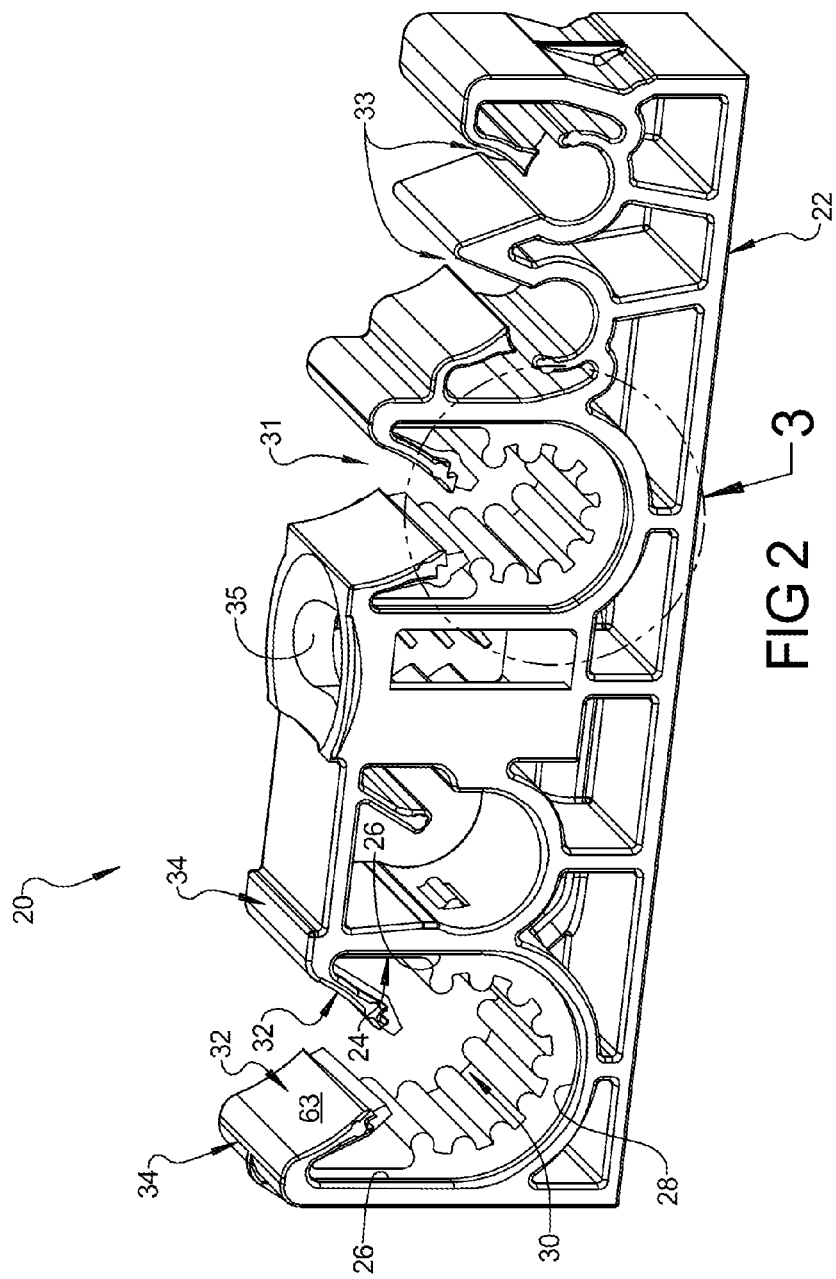
FIG. 2 is a perspective view of the two-shot tube retention pocket tube clamp of FIG. 1, including an enlarged portion illustrating a band, set-back, or notch.
Figure 3:
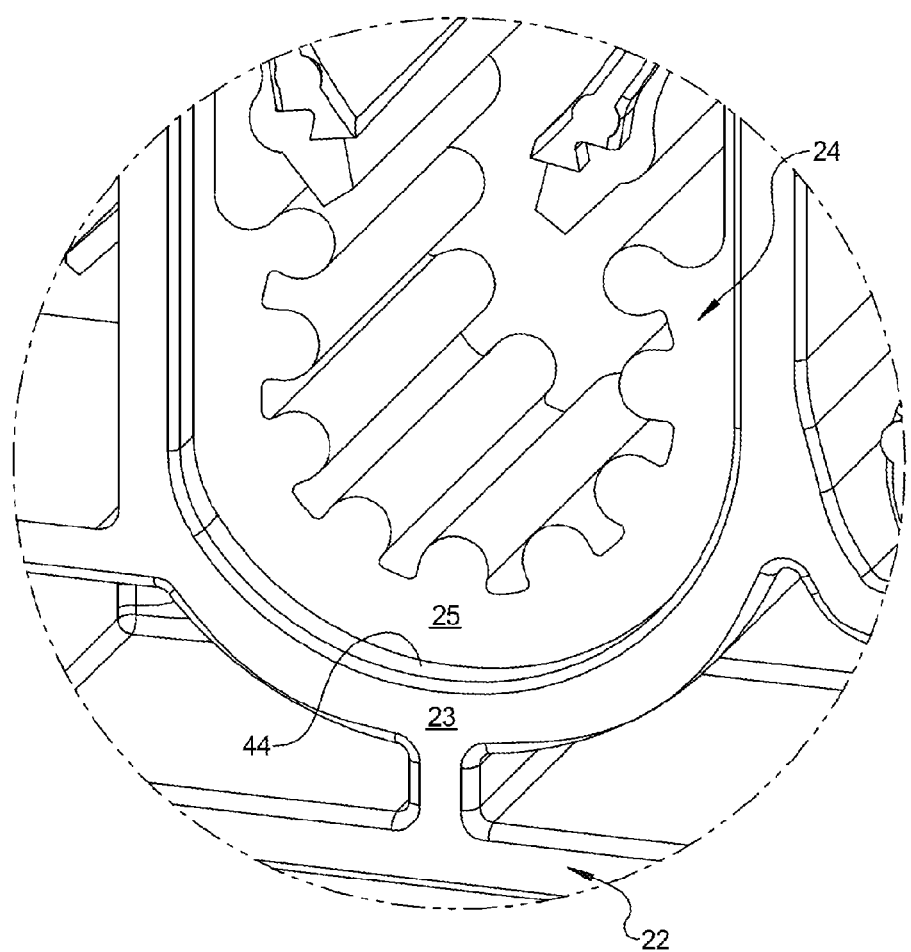
FIG. 3 is an enlarged portion of FIG. 2.

Example embodiments will now be described more fully with reference to the accompanying drawings.

Referring to FIGS. 1-6, one exemplary tube retention fastener 20 in accordance with the present disclosure is illustrated. The tube retention fastener 20, includes a body 22 that is made of a first, relatively rigid polymeric material, and an isolation member 24 that is made of an elastically resilient second material. The tube retention fastener 20 can be molded using a two-shot molding process in which the body 22 is molded during a first shot, and then the isolation or second shot member 24 is molded in a second shot so that the isolation member 24 is coupled to and against surfaces of the body or first shot member 22.

The tube retention fastener 20 includes a pair of side walls 26 with a semi-circular sleeve 28 positioned between the side walls 26. As illustrated, the side walls 26 and semi-circular sleeve 28 in combination can define a U-shaped longitudinal pocket 30. The tube retention fastener 20 includes a pair of deflecting wings 32. Each deflecting wing 32 is coupled to one of the side walls 26 forming a corner 34. Each deflecting wing 32 having a non-deflected position in which the deflecting wing 32 angularly extends from the respective side wall 26 toward a central longitudinal axis 39 of the U-shaped longitudinal pocket 30.

Each deflecting wing 32 further includes a portion of the isolation member 24 bonded to an interior surface 38 of the deflecting wing 32. As illustrated, the isolation member 24 can be bonded to a continuous portion of the interior surface 38 of each deflecting wing 32 that extends from a distal end 40 of each deflecting wing 32 to its corner 34 or junction with its side wall 26. The continuous portion of the interior surface 38 of the body 22 to which the isolation member is bonded can further extend from each corner 34 over each of the side walls 26 and over the semi-circular sleeve 28. Thus, each corner 34 can define a hinge point for both the body 22 portion and the isolation member 24 portion bonded at the corner 34 to the body 22 portion of the deflecting wing 34.

All or part of the exterior surface 42 of the deflecting wings 32 can be free of the isolation member 24. A portion of the interior surface 38 of the longitudinal pocket 30 of the body 22 can be free of the isolation member 24. As seen best in FIG. 3, this isolation member-free portion 44 of the interior surface 38 can be an outer band, offset, or notch 44 adjacent the longitudinal end, edge or face 46 of the body 22. The outer band, offset, or notch 44 can provide the front longitudinal end face 25 of the isolation member 24 that is set-back relative to the front longitudinal end face 23 of the body member 22. A similar isolation member-free portion 44 of the interior surface 38, which can be in the form of a set-back, band, or notch 44, can also be provided at the opposite longitudinal end, edge, or opposing back face 46 of the body 22.

Such an isolation member-free portion or portions 44 of the interior surface 38 can be limited to the deflecting wings 32; that is, between the distal end 40 and its corner 34. As illustrated, an isolation member-free portion or portions 44 of the interior surface 38 can also be provided adjacent the side walls 26; that is, between the corners 34 and the semi-circular sleeve 28. Similarly, an isolation member 24 free portion or portions of the interior surface 38 can also be provided on the semi-circular sleeve 28; that is, between the side walls 26. As illustrated, the isolation member-free portion 44 can extend continuously adjacent an isolation member 24 that is continuously bonded from the distal end of each wing 32, to each adjacent corner 34, throughout each adjacent side wall 26, and throughout the semi-circular sleeve 28.

Figure 4:
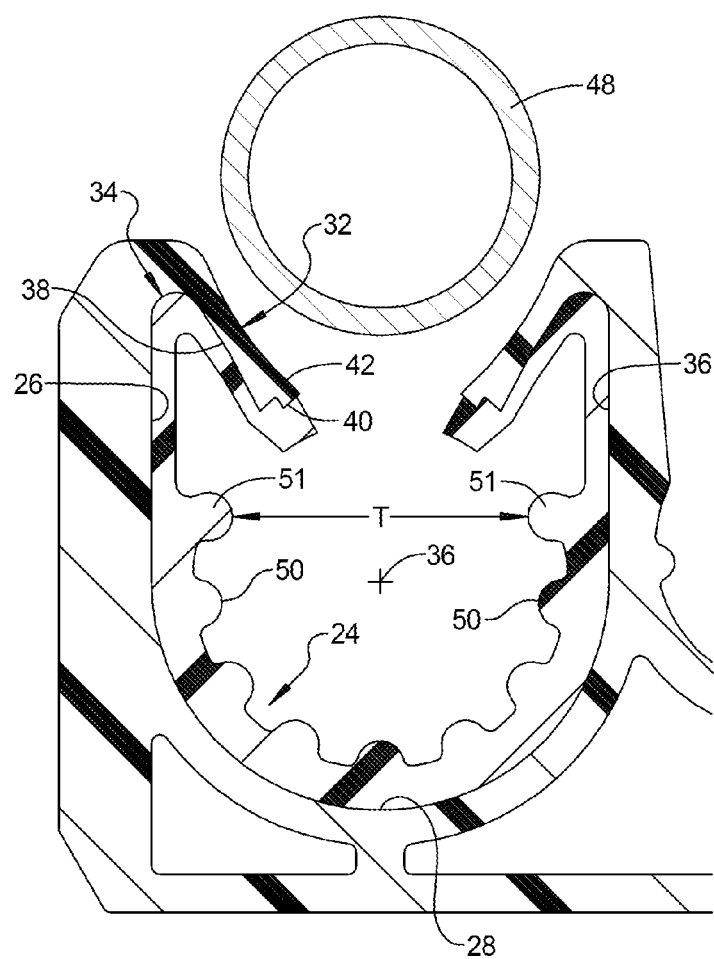
FIG. 4 is a partial cross-sectional view of the two-shot tube retention pocket tube clamp and a tube prior to insertion into the pocket.
Figure 5:
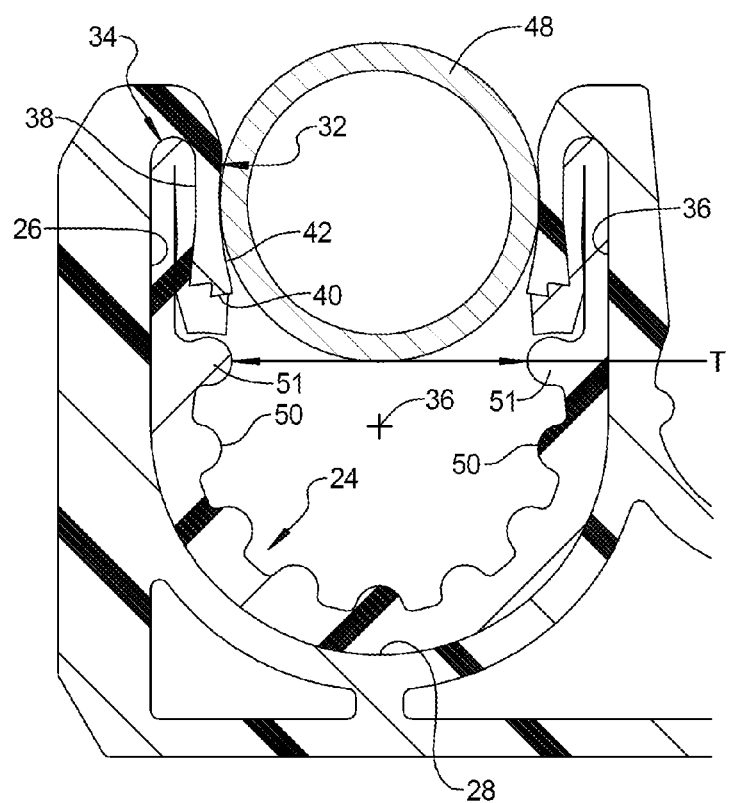
FIG. 5 is a partial cross-sectional view similar to FIG. 4, with the tube being inserted into the pocket.
Figure 6:
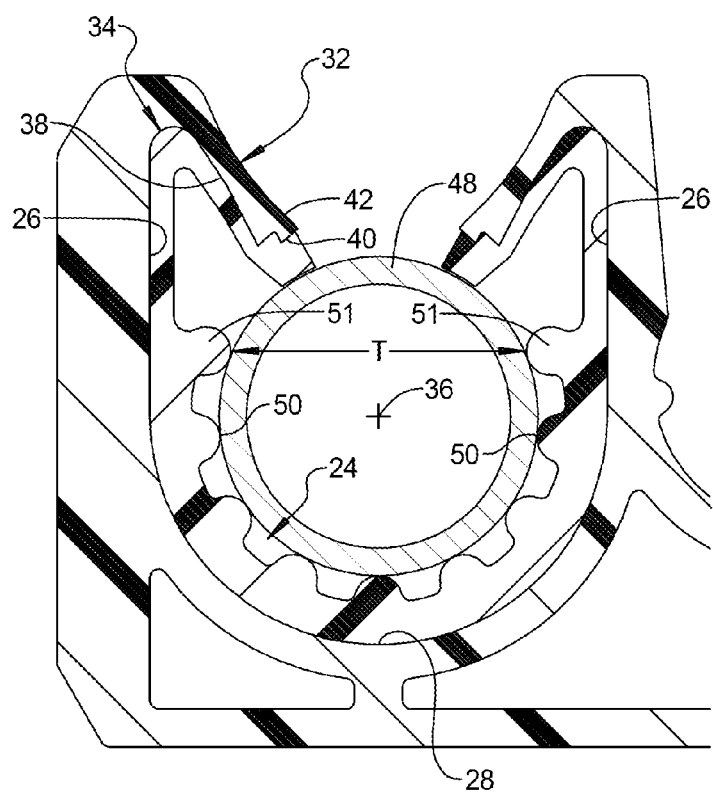
FIG. 6 is a partial cross-sectional view similar to FIG. 4, with the tube fully seated in the pocket.

Referring to FIGS. 4-6, showing a tubular member 48 prior to insertion into, during insertion into, and after insertion into the longitudinal pocket 30 of the tube retention fastener 20, respectively. During insertion, as seen in FIG. 5, each deflecting wing 32 is able to fold flat against the side wall 26 to which the deflecting wing 32 is directly coupled. As illustrated, the portion of the isolation member 24 bonded to the interior surface of each deflecting wing 32 is able to engage the portion of the isolation material 24 bonded to the interior surface of the adjacent side wall 26 in a face-to-face orientation along the entire length of the deflecting wing 32. The isolation member 24 includes a pre-molded corner 34. There is no need to create a corner or bend in the isolation material 24 as the deflecting wings 32 move from a non-deflected position such as shown in FIG. 4 into a deflected position shown in FIG. 5.

In addition, there is no open space required between the deflecting wing 32 and the adjacent side wall 26. As seen in FIG. 5, each of the pair of deflecting wings 32 has a deflected position in which a wing portion of the isolation member 24 that is bonded to each deflecting wing 32 along a first span between a corner 34 and a distal end 40 of the deflecting wing 32 can contact in a face-to-face relationship against a side wall 36 portion of the isolation member 24 that is bonded to an adjacent side wall 36 along a second span between the corner 34 and the semi-circular sleeve 28. The illustrated configuration enables the distance between the side walls 26 to be reduced or minimized for any desired tubular member 48 diameter or throat opening size or distance between the deflecting wings 32 in their deflected positions.

The isolation member 24 includes a series of interior longitudinal ribs 50 extending longitudinally around the longitudinal tube holding pocket 30. The uppermost ribs 51 (relative to the deflecting wings 32) can define an entry throat T that is narrower than a diameter defined by the plurality of longitudinal ribs 50. These uppermost longitudinal ribs 51 are also above the longitudinal axis 36 defined by the remaining ribs 50, are adjacent the side wall 26 instead of the semi-circular sleeve 28, and have a height dimension or form a thickness of the isolation member 24 that is larger than the height of or thickness formed at the other longitudinal ribs 50 below the longitudinal axis 36. In addition to defining the entry throat opening T, the uppermost longitudinal ribs 51 operate to center the tubular member 48 in the longitudinal tube holding pocket 30 during insertion.

The tube retention fastener 20 can include a second tube retention pocket 31 having all or some combination of similar features to those illustrated and described in relation to retention pocket 30. The body 22 can include a flow channel 49 which can provide a passageway allowing the elastically resilient isolation material to flow between or to both pockets 30, 31 during the second shot molding of the isolation member 24 for each pocket 30, 31. The tube retention fastener 22 can include other features including tube retention pockets 33 without any associated elastically resilient isolation material or member 24, and a fastener opening 35 structured to receive a fastener, such as a threaded fastener.

Figure 7:
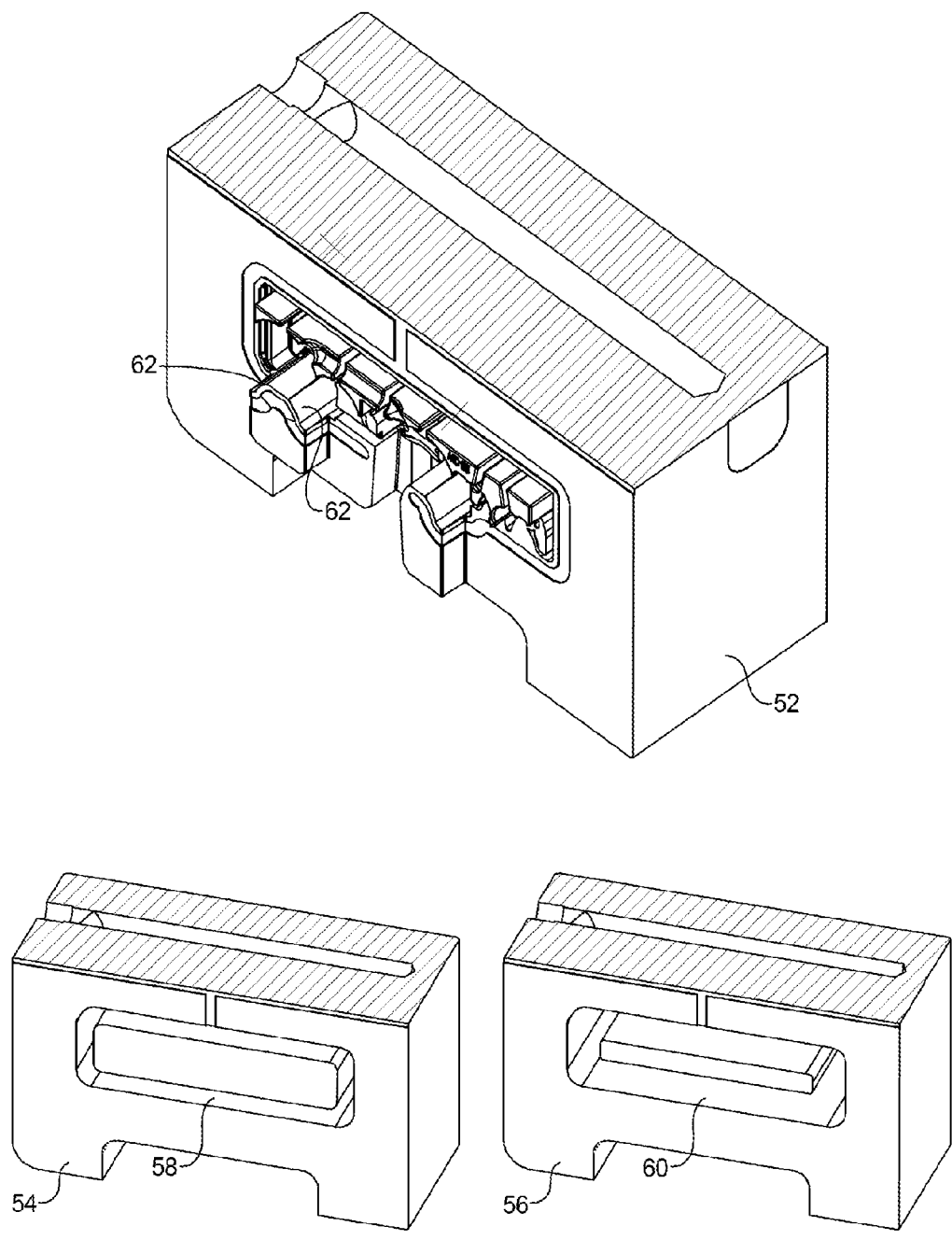
FIG. 7 is a partial perspective view of a first mold member for forming the two-shot tube retention pocket tube clamp of FIG. 1 and perspective illustrations representing second and third mold members.
Figure 8:
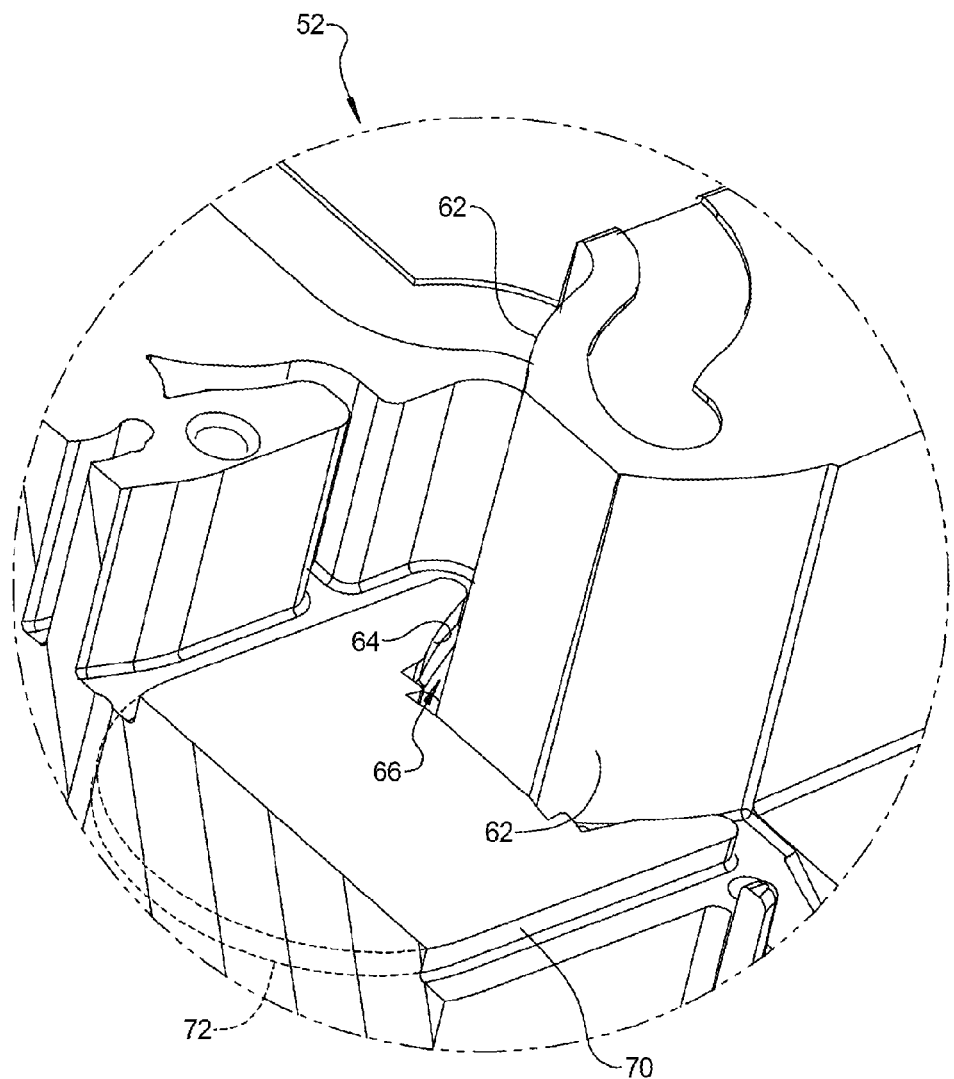
FIG. 8 is an enlarged partial cross-sectional view of the first mold member of FIG. 7.
Figure 9:
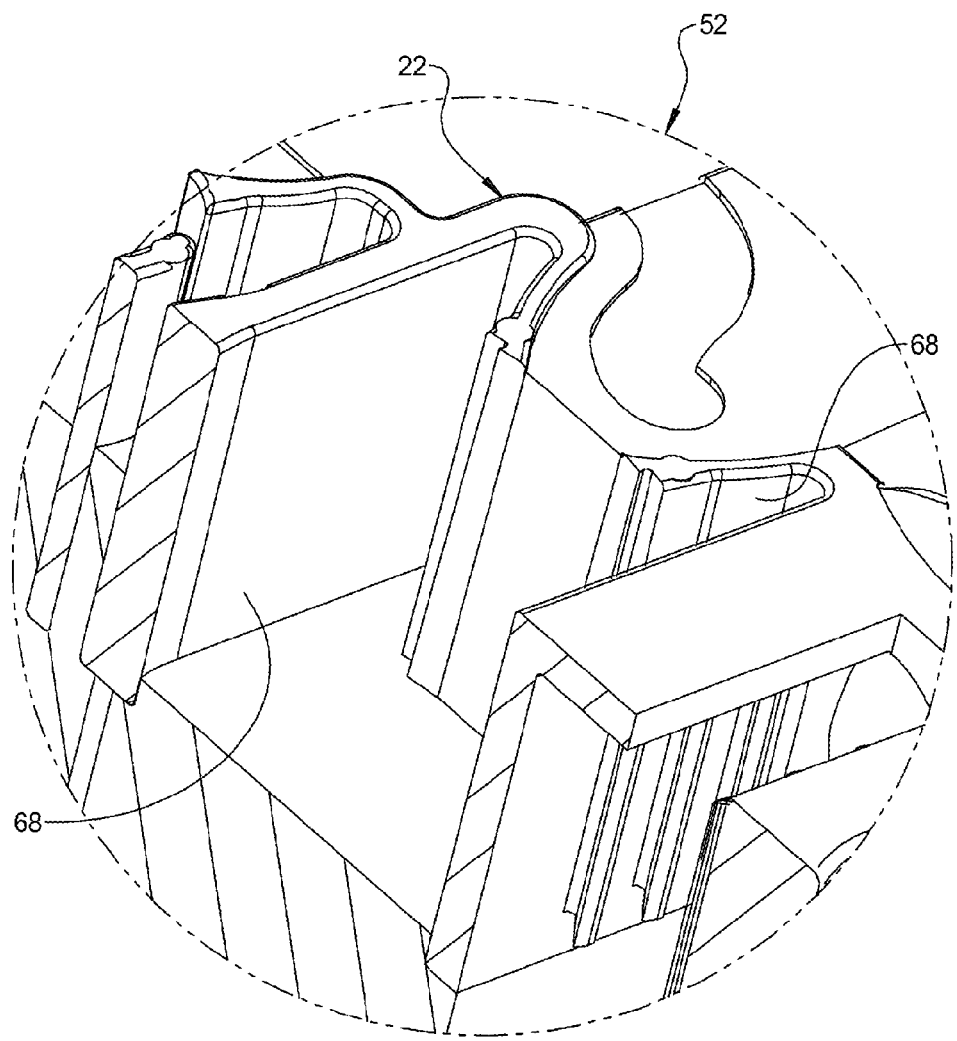
FIG. 9 is an enlarged partial cross-sectional view similar to FIG. 8, including a corresponding portion of the body member formed using the first and second mold members.

Referring to FIGS. 7-9, three mold members 52, 54, and 56 are provided for molding a two-shot tube retention fastener 20 such as exemplified above. The first mold member 52 is positioned or mated with the second mold member 54 to form a first shot cavity 58 that defines the body or first shot member 22. This first shot cavity 58 is represented in FIG. 7 as an annular recess that is narrow, since it combines with the first mold member 52 to define the thickness of only the first shot member 22. The first mold member 52 is positioned or mated with the third mold member 56, with the first shot member 22 remaining with the first mold member 52, to form a second shot cavity 60 that defines the isolation or second shot member 24. This second shot cavity 60 is represented in FIG. 7 as an annular recess that is wider, since it combines with the first mold member 52 to define the second shot member 24 while accounting for the presence of the first shot member 22 within the mold pair 52 and 56.

The first mold member 52 includes a pair of surfaces 62 that each form the outer surface 63 of the body member 22 portion of the wings 32. This outer surface 63 is oppositely disposed to the interior surface 38 of the wings 32 to which the isolation member 24 is bonded. Each surface 62 of the first mold member 52 can remain in contact with the outer surface 63 of the corresponding wing 32 of the first shot body member 22 once formed, until after completion of the second shot operation forming the second shot isolation member 24 against the interior surface 38 of the wings 32 of the first shot body member 22. Thus, the pair of mold surfaces 62 can provide support for the wings 32 during the second shot molding operation so that the first shot body member portion of the wings 32 do not disadvantageously deflect while molding the second shot isolation member 24 to the interior surface 38 of the wings 32. As a result, the second shot molding operation can be performed more quickly and prior to complete cooling of the relatively rigid polymeric material forming first shot body member 22.

The first mold member 52 can also include a surface 64 for each wing 32 that contacts against a longitudinal edge or band 44 of the interior surface 38 of the wings 32 of the first shot body member 22. Portions of the interior surface 38 of the wings 32 of the first shot body member 22 are left unsupported, so the unsupported interior surface 38 defines a portion of the mold cavity 58 of the second shot member 24 that can extend from a distal end of the wings 32 through to the adjacent corner 34 or pair of side walls 26 of the first shot body member 22.

The interior first shot member wing supporting surface 64 and part of the exterior first shot member wing supporting surface 62 can be provided in the first mold member 52 by a groove 66 in the first mold member 52. As should be apparent from the discussion above, the outer band, setback, or notch 44 adjacent the longitudinal end, edge or face 46 of the body 22 can result from the interior first shot member wing supporting surface 64 or groove 66 of the first mold member 52. The third mold member 56 in combination with the first mold member 52 and the first shot body member 22 can define a second shot member 24 cavity 60 partially defined by an exposed bonding surface 68 of the first shot member 22 continuously extending from a distal end 40 of each deflecting wing 32 to the adjacent corner 34.

The first mold member 52 can include surfaces 70 and 72 that similarly support respective interior portions of the side walls 26 and the semi-circular sleeve 28, respectively. Some or all of these interior supporting surfaces 64, 70, and 72, can extend continuously from each other and/or can be associated with a groove 66. The exposed bonding surface 68 of the first shot member 24 can extend continuously from a distal end a deflecting wing 32, over the deflecting wing 32, over the adjacent side wall 26, over the semi-circular sleeve 28, over the other side wall 26, over and to a distal end 40 of the other deflecting wing 32.

Corresponding or oppositely disposed interior first shot member wing supporting surface 62 can be provided as part of the third mold member 56 to support the wing 32 at its opposite longitudinal end, edge, or face 46 forming a corresponding opposite outer band, set-back, or notch 44. Similarly, corresponding or oppositely disposed interior supporting surfaces 70 and 72 can be provided on the third mold member. Likewise, the exposed bonding surface 68 can continuously extend over the side walls 26 and semi-circular sleeve 28 portions of the first shot body member 24 as well.

Two-shot tube retention fastener molding methods should be apparent from the above. For example, a first shot body member 24 including a pair of deflecting wings 32 can be molded by combining a first mold member 52 and a second mold member 54 to form a first shot body member cavity 58. The first mold member 52 holding the first shot body member 22 can be combined with a third mold member 56 to form a second shot body member cavity 60. During the molding of the second shot isolation member 24 an exterior wing surface of each deflecting wing 32 can be supported by a surface 62 of the first mold member 52. In addition, during the second shot molding operation, a surface 64 of the first mold member 52 can also support interior wing surface portions of each of the pair of deflecting wings 32, while leaving an interior wing bonding surface 68 exposed to define a portion of the second shot isolation member cavity 60.

Interior portions of the side walls 26 and semi-circular sleeve 28 of the first shot body member 22 can also be supported by surfaces 70 and 72 of the first mold member 52 during molding of the second shot isolation member 24. Molding the second shot isolation member 24 can also involve supporting corresponding interior surfaces at the opposite longitudinal end of the pocket 31 by providing corresponding surfaces 64, 70, and 72 on the third mold member 60. As previously described, the exposed bonding surface 68 defining the second shot cavity 60 can continuously extend over the entire length of any or all of the wings 32, the corner 34, the side walls 26, and the semi-circular sleeve 28.

Example embodiments are provided so that this disclosure will be thorough, and will fully convey the scope to those who are skilled in the art. Numerous specific details are set forth such as examples of specific components, devices, and methods to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only, and is not intended to be limiting. The method steps, processes, and operations described herein are not to be construed as necessarily requiring their performance in the particular order discussed or illustrated, unless specifically identified as an order of performance. It is also to be understood that additional or alternative steps may be employed.

Although the terms first, second, third, etc., may be used herein to describe various elements, components, regions, layers and/or sections, these elements, components, regions, layers and/or sections should not be limited by these terms.

These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

The foregoing description of the embodiments has been provided for purposes of illustration and description. It is not intended to be exhaustive or to limit the disclosure. Individual elements or features of a particular embodiment are generally not limited to that particular embodiment, but, where applicable, can be combined with any combination of features of other embodiments, even if not specifically shown or described. The same may also be varied in many ways. Such variations are not to be regarded as a departure from the disclosure, and all such modifications are intended to be included within the scope of the disclosure.

What is claimed is:

1. A tube retention fastener, comprising:
    a body of a first polymeric material, the body including:
        a pair of side walls;
        a semi-circular sleeve positioned between the pair of side walls to define a portion of a longitudinal pocket;
        a pair of deflecting wings, each of the pair of deflecting wings being coupled to one of the pair of side walls at one of a pair of corners, respectively, each deflecting wing extending toward a central plane passing through a longitudinal axis of the longitudinal pocket in a non-deflected position;
        wherein the pair of side walls, the semi-circular sleeve, the pair of corners, and the pair of deflecting wings together define an interior surface of the longitudinal pocket;
    an isolation member of an elastically resilient second material bonded to portions of the interior surface of the longitudinal pocket defined by each of: the semi-circular sleeve, each of the pair of side walls, each of the pair of corners, and each of the pair of deflecting wings;
        wherein each of the deflecting wings includes a first portion of the isolation member bonded to each of the deflecting wings and defining a wing face between a distal end of each of the deflecting wings and a respective one of the corners, and
    wherein each of the side walls includes a second portion of the isolation member bonded to each of the side walls and defining a side wall face opposing the wing face between the distal end of each of the deflecting wings and a respective one of the corners, and wherein each one of the pair of corners defines a hinge point for both an isolation member portion and a body portion of an adjacent one of the pair of deflecting wings.

2. The tube retention fastener of claim 1, wherein each of the pair of deflecting wings has a deflected position in which the wing face of the isolation member contacts against the side wall face of the isolation member.

3. The tube retention fastener of claim 1, wherein a wing longitudinal end face of the isolation member is interiorly offset from a wing longitudinal end face of the body adjacent each of the pair of deflecting wings.

4. The tube retention fastener of claim 3, wherein the wing longitudinal end face of the isolation member is interiorly offset from the wing longitudinal end face of the body adjacent an entire wing length of each of the pair of deflecting wings from the respective first and second corner to the respective first and second distal ends.

5. The tube retention fastener of claim 1, wherein a longitudinal end face of the isolation member is interiorly offset from a longitudinal end face of the body adjacent an entire longitudinal pocket length from the first corner along the first side wall, the semi-circular sleeve, and the second side wall to the second corner.

6. The tube retention fastener of claim 1, wherein the resilient member further comprises a plurality of longitudinal ribs within the longitudinal pocket, and wherein a pair of opposing longitudinal ribs define an entry throat that is narrower than a diameter defined by the plurality of longitudinal ribs.

7. The tube retention fastener of claim 6, wherein each of the pair of deflecting wings has a deflected position in which a distance between outer surfaces of each of the deflecting wings is larger than the entry throat.

8. The tube retention fastener of claim 1, wherein the distal end of each deflecting wing has a disruptive shape with the isolation member bonded thereto.

9. The tube retention fastener of claim 8, wherein the disruptive shape comprises a "Z" shaped surface.

10. A tube retention fastener, comprising:
    a body of a first polymeric material, the body including:
        a pair of side walls;
        a semi-circular sleeve positioned between the pair of side walls to define a portion of a longitudinal pocket;
        a pair of deflecting wings, each of the pair of deflecting wings being coupled to one of the pair of side walls at one of a pair of corners, respectively, each deflecting wing extending toward a central plane passing through a longitudinal axis of the longitudinal pocket in a non-deflected position;
        wherein the pair of side walls, the semi-circular sleeve, the pair of corners, and the pair of deflecting wings together define an interior surface of the longitudinal pocket;
    an isolation member of an elastically resilient second material bonded to portions of the interior surface of the longitudinal pocket defined by each of: the semi-circular sleeve, each of the pair of side walls, each of the pair of corners, and each of the pair of deflecting wings;
        wherein a wing longitudinal end face of the isolation member is interiorly offset from an adjacent wing longitudinal end face of the body to expose a lip of the portion of the interior surface defined by each of the pair of deflecting wings of the body.

11. The tube retention fastener of claim 10, wherein each one of the pair of corners defines a hinge point for both an isolation member portion and a body portion of an adjacent one of the pair of deflecting wings.

12. The tube retention fastener of claim 10, wherein the resilient member further comprises a plurality of longitudinal ribs within the longitudinal pocket, and wherein a pair of opposing longitudinal ribs define an entry throat that is narrower than a diameter defined by the plurality of longitudinal ribs.

13. The tube retention fastener of claim 12, wherein each of the pair of deflecting wings has a deflected position in which a distance between outer surfaces of each of the deflecting wings is larger than the entry throat.

14. The tube retention fastener of claim 10, wherein a distal end of each deflecting wing has a disruptive shape with the isolation member bonded thereto.

15. The tube retention fastener of claim 14, wherein the disruptive shape comprises a "Z" shaped surface.

16. A tube retention fastener, comprising:
a body of a first polymeric material, the body including:
a pair of side walls;
a semi-circular sleeve positioned between the pair of side walls to define a portion of a longitudinal pocket;
a pair of deflecting wings, each of the pair of deflecting wings being coupled to one of the pair of side walls at one of a pair of corners, respectively, each deflecting wing extending toward a central plane passing through a longitudinal axis of the longitudinal pocket in a non-deflected position;
wherein the pair of side walls, the semi-circular sleeve, the pair of corners, and the pair of deflecting wings together define an interior surface of the longitudinal pocket;
an isolation member of an elastically resilient second material bonded to portions of the interior surface of the longitudinal pocket defined by each of: the semi-circular sleeve, each of the pair of side walls, each of the pair of corners, and each of the pair of deflecting wings;
wherein each of the deflecting wings includes a first portion of the isolation member bonded to each of the deflecting wings and defining a wing face between a distal end of each of the deflecting wings and a respective one of the corners, and wherein each of the side walls includes a second portion of the isolation member bonded to each of the side walls and defining a side wall face opposing the wing face between the distal end of each of the deflecting wings and a respective one of the corners; and
wherein a wing longitudinal end face of the isolation member is interiorly offset from an adjacent wing longitudinal end face of the body to expose a lip of the portion of the interior surface defined by each of the pair of deflecting wings of the body.

17. The tube retention fastener of claim 16, wherein each one of the pair of corners defines a hinge point for both an isolation member portion and a body portion of an adjacent one of the pair of deflecting wings.

18. The tube retention fastener of claim 16, wherein each of the pair of deflecting wings has a deflected position in which the wing face of the isolation member contacts against the side wall face of the isolation member.

19. The tube retention fastener of claim 16, wherein the wing longitudinal end face of the isolation member is interiorly offset from the wing longitudinal end face of the body adjacent an entire wing length of each of the pair of deflecting wings from the respective first and second corner to the respective first and second distal ends.

20. The tube retention fastener of claim 16, wherein the resilient member further comprises a plurality of longitudinal ribs within the longitudinal pocket, and wherein a pair of opposing longitudinal ribs define an entry throat that is narrower than a diameter defined by the plurality of longitudinal ribs.

21. The tube retention fastener of claim 20, wherein each of the pair of deflecting wings has a deflected position in which a distance between outer surfaces of each of the deflecting wings is larger than the entry throat.

22. The tube retention fastener of claim 16, wherein the distal end of each deflecting wing has a disruptive shape with the isolation member bonded thereto.

23. The tube retention fastener of claim 22, wherein the disruptive shape comprises a "Z" shaped surface.

* * * * *